(12) United States Patent
Ishikawa et al.

(10) Patent No.: US 7,348,586 B2
(45) Date of Patent: Mar. 25, 2008

(54) EXTERIOR ELEMENT SENSOR

(75) Inventors: Kiyomitsu Ishikawa, Tokyo (JP); Hiroshi Takata, Tokyo (JP)

(73) Assignee: Stanley Electric Co. Ltd., Tokyo (JP)

( * ) Notice: Subject to any disclaimer, the term of this patent is extended or adjusted under 35 U.S.C. 154(b) by 0 days.

(21) Appl. No.: 11/172,818

(22) Filed: Jul. 5, 2005

(65) Prior Publication Data

US 2006/0006318 A1  Jan. 12, 2006

(30) Foreign Application Priority Data

Jul. 12, 2004 (JP) ............................. 2004-204789

(51) Int. Cl.
*G01N 15/06* (2006.01)

(52) U.S. Cl. .................. 250/573; 250/227.25; 318/480

(58) Field of Classification Search ........ 250/573–575, 250/227.25, 216, 341.8; 318/480, 483

See application file for complete search history.

(56) References Cited

U.S. PATENT DOCUMENTS 6,376,824 B1 * 4/2002 Michenfelder et al. . 250/214 R

FOREIGN PATENT DOCUMENTS

JP  2001-066246  3/2001

\* cited by examiner

*Primary Examiner*—Kevin Pyo
(74) *Attorney, Agent, or Firm*—Cermak Kenealy & Vaidya LLP

(57) ABSTRACT

An exterior element sensor can include an optical element mounted on a window. The optical element can include a cylindrical lens having both ends shaped spherically and a central portion that exerts little or no influence on exterior element detection (such as rain, snow, ice, water, liquid, debris, or other materials) when visible light transmits therethrough. In addition, infrared or other light can be used to detect exterior elements located on the window. A black filter can be employed, if desired, which blocks visible light and transmits infrared light therethrough to separate visible light from infrared light, thereby allowing the exterior element sensor to be used together with an exterior light sensor without losing accuracy.

20 Claims, 2 Drawing Sheets

EXTERIOR ELEMENT SENSOR

This invention claims the benefit of Japanese patent application No. 2004-204789, filed on Jul. 12, 2004, which is hereby incorporated by reference.

BACKGROUND OF THE INVENTION

1. Field of the Invention

The invention relates to an exterior element sensor for detecting elements such as rain, snow, water, liquids, dirt and other debris on a window. In particular, the invention relates to an exterior element sensor which can be mounted on a surface such as a window, an automobile windshield, or other structure that loses its field of vision when enough raindrops or other exterior elements contact its surface. The exterior element sensor can be employed to automatically operate wipers when a predetermined amount of exterior elements such as raindrops, snow, water, debris, etc. are detected on the window or windshield. Together with the exterior element sensor of this type, a light sensor is often provided to automatically turn on/off headlights or other devices in response to variations in surrounding brightness at sunset or on access to a tunnel and evacuation therefrom, during rain, snow, or other circumstances.

2. Description of the Related Art

A typical configuration for an exterior element sensor of this type in the art is shown in FIG. 6. In this case, an incident optical element 11a is attached to an interior surface of a window W such as a front window via a right prism with an apex of 90° facing upward, using a transparent adhesive 14 such as an epoxy resin. The configuration yields a surface angled at 45° to the window surface. Light from a light-emitting element such as an LED is emitted into the angled surface at a right angle thereto.

Thus, the light coming into the surface of the window W from the incident optical element can pass into the window W without suffering refraction due to a difference between refractive indexes of the atmosphere and the window. Even when the light reaches an exterior surface Wo of the window, the angle of 45° (which is larger than the critical angle) can be held. Therefore, in the exterior surface Wo of the window, total reflection arises at an inner surface of the window.

When total reflection occurs at the inner surface of the window in this way, an angle of incidence is the same as an angle of reflection. Accordingly, the light that is totally reflected from the exterior surface Wo of the window is folded back and reaches either the interior surface Wi of the window W or a high refractive index plane that is in parallel with the interior surface from which it is totally reflected. Thereafter, similar total reflection is repeated between the exterior surface and the interior surface, alternately. Thus, the light is confined within the window W.

Provided therefore is an emissive optical element 11b. This emissive optical element 11b includes a right prism, which is configured the same as that of the incident optical element 11a and is similarly adhered onto the inner surface of the window W with a transparent resinous adhesive, for example. The place of adhesion is a location on the interior surface Wi of the window, to which the light coming into the incident optical element 11a returns, after it is totally reflected at least once from the exterior surface Wo of the window W. In general, the incident optical element 11a and the emissive optical element 11b are integrated into a sensing optical element 11 in consideration of the thickness and the critical angle of the window W, and both can be arranged in place in one adhesion work.

Thus, the light coming into the incident optical element 11a and totally reflected at least once from the exterior surface Wo of the window can exit from the emissive optical element 11b. The amount of this light is always observed at a photoreceptor 13. In this case, if raindrops are attached to the exterior surface Wo of the window during a rainfall, for example, since the window and the raindrops (water) can have approximately the same refractive indexes, shape variations may occur in the reflecting surface. In this state, the resultant leakage of light and diffused reflection reduces the amount of light observed at the photoreceptor 13, which can thus detect the amount of raindrops, or the rainfall. Though it is not shown in FIG. 6, in vehicles in which detected rainfall automatically controls wipers, an exterior light sensor may often be provided separately to turn on/off the light depending on the external brightness (Please see Japanese Patent Document JP-A 2001-66246, for example).

In the above conventional configuration, however, the raindrop sensor requires a light source. As shown in FIG. 1, the exterior element sensor is not configured to consider the joint use of sensing exterior light, of the related art (see Japanese Patent Document JP-A 2001-66246). Therefore, the exterior element sensor and the exterior light sensor are provided separately. Accordingly, the sensors are often provided at two locations on the front of the windshield, which blocks a large field of vision, resulting in a problem in that the driver of the vehicle experiences an increase in lost field of vision.

Providing the exterior element sensor and the exterior light sensor separately requires respective special-purpose lenses, cases, and circuit components, which increases the number of components and the steps of assembling. Thus, increasing management and production problems, which inevitably elevates the overall cost of production.

Furthermore, when the incident optical element 11a and the emissive optical element 11b are adhered onto the window W, a positional relation between both requires accuracy. Therefore, as shown in FIG. 6, a prism body 11c must be formed in the shape of two right prisms connected at a certain interval to each other, requiring a high process technology and further increasing the cost.

SUMMARY OF THE INVENTION

The invention provides an exterior element sensor that can solve the above and other conventional problems in the art. In accordance with an aspect of the invention, the exterior element sensor can detect various elements, including raindrops, snow, ice, liquid, debris, etc., and thereafter activate any number of devices. The exterior element sensor can include a sensing optical element, which includes a connection portion having one end portion serving as an incident optical element portion and the other end portion serving as an emissive optical element portion and which is adhered with a resinous adhesive or the like to an interior surface of a window. The window can be made from glass, resin, plastic, or other similar material. An infrared LED or other light source can be mounted opposite to the incident optical element portion at a location that allows light from the infrared LED to be totally reflected from the exterior surface of the window. A first photoreceptor can be mounted opposite to the emissive optical element portion at a location such that it can receive the light that is totally reflected from the exterior surface of the window. A second photoreceptor serving as an exterior light sensor can be mounted at a location opposite to the center of the connection portion between the incident optical element portion and the emissive optical element portion. Thus, an exterior element sensor according to this aspect can be firstly effective to simplify the shape of the sensing optical element.

Secondly, a connection portion that connects the incident optical element portion and the emissive optical element portion can be left as a portion not serving to sense exterior elements, and which can be employed as a lighting portion of the exterior light sensor. Thus, the incident optical element portion and the emissive optical element portion can be integrated together for downsizing, and reducing components and steps of production.

As described above, the configuration of the sensing optical element can be intended to simplify the shape of the device. Additionally, in the sensing optical element, the connection portion that connects the incident optical element portion and the emissive optical element portion can be left as a portion that does not serve to sense exterior elements. Further, this portion can be employed to locate the second photoreceptor serving as the exterior light sensor to integrate the exterior element sensor with the exterior light sensor. Thus, extremely effective downsizing resulting in the reduction in components, production steps and costs can be realized.

BRIEF DESCRIPTION OF THE DRAWINGS

These and other features and advantages of the invention will become clear from the following description with reference to the accompanying drawings, wherein.

DETAILED DESCRIPTION OF PREFERRED EMBODIMENTS

Figure 1:
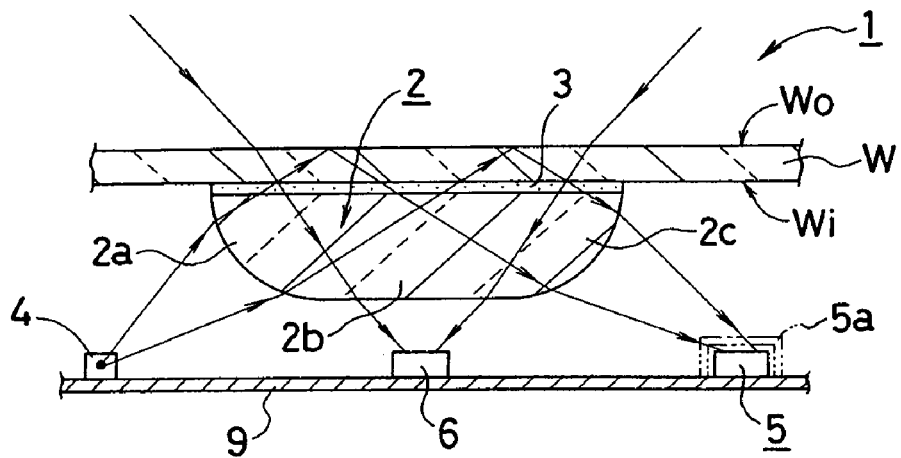
FIG. 1 is a cross-sectional view showing an embodiment of an exterior element sensor made in accordance with the principles of the invention.

The invention will now be described in detail on the basis of the exemplary embodiments shown in the figures. FIG. 1 shows an embodiment of an exterior element sensor 1 made in accordance with the principles of the invention, including a sensing optical element 2. The sensing optical element 2 can be formed in the shape of a half of a cylinder having both ends shaped hemispherically and equally divided into two at the central axis and, as shown in FIG. 1, can be composed of transparent glass, transparent resinous material, or the like.

In the sensing optical element 2 formed as described above, a connection portion 2b that is in the shape of a semicircular cylindrical lens in section can be provided. Quarter-spherical lenses can be provided at either end of the semicircular cylindrical lens. One of these lenses at both ends can be employed as an incident optical element portion 2a and the other as an emissive optical element portion 2c.

The sensing optical element 2 can be mounted with a transparent resinous adhesive 3 or the like onto an interior surface Wi of a window W, such as a vehicle window or windshield. The window W can be made from glass, resin, plastic, or other similar material. In this case, the sensing optical element 2 and the resinous adhesive 3 are selected from commonly available materials having refractive indexes of about 1.4-1.5, which is close to the refractive index for the window W, to reduce refraction and reflection at a contact plane between them.

It is intended that total reflection occurs at an exterior surface Wo of the window W when no raindrops (or other exterior elements) are located adjacent the sensing optical element 2 mounted on the interior surface Wi of the window W. Under this condition, light is led into the incident optical element portion 2a. An infrared LED 4 or other type of lamp can be used as a light source.

When it is intended to lead infrared light into the sensing optical element 2, the infrared LED 4 may be located at or near the focal position of the incident optical element portion 2a. In this case, the light emitted from the infrared LED 4 enters the incident optical element portion 2a, and then it is collimated, and travels inside the sensing optical element 2. Therefore, the infrared LED 4 may be located at an appropriate position on or near the focus of the incident optical element portion 2a. In this case, the light emitted from the infrared LED 4 transmits through the resinous adhesive 3 and reaches the exterior surface Wo of the window W at an angle larger than the critical angle to achieve the condition required for total reflection.

Accordingly, the connection portion 2b can be set to have an appropriate length so that the infrared light that is totally reflected from the exterior surface Wo of the window W reaches the emissive optical element portion 2c. In this case, the infrared light can be converged and focused when it is radiated from the emissive optical element portion 2c to the interior atmosphere. Therefore, a first photoreceptor 5 may be located on the focal position to measure the amount of light which is emitted from the infrared LED 4, and which then transmits though the sensing optical element 2, and which is then reflected from the exterior surface Wo of the window W.

In the case when the exterior element sensor is used to detect rainfall, raindrops that occur during a rainfall attach to the exterior surface Wo of the window W and cause leakage of this reflected light. As raindrops increase, the output from the first photoreceptor 5 gradually decreases so that the state/number of raindrops that are located on the window W can be calculated. Accordingly, if the speed at which the amount of light decreases is slow, wipers can be driven in accordance with the state of the rainfall, for example, driven as intermittent wipers.

The above description has been given to the configuration and operation of the sensing optical element 2 configured as the exterior element sensor 1. In addition to the above configuration, at the center in the axial direction of the connection portion 2b on the side in which the shape of the cylindrical lens protrudes, a second photoreceptor 6 can be provided at an appropriate spacing therefrom.

The light coming into the second photoreceptor 6 is herein described. Light from outside of the window W or windshield of the vehicle enters through the exterior surface Wo of the window W, then transmits through the connection portion 2b of the sensing optical element 2, and finally reaches the second photoreceptor 6. Namely, this outside light is referred to as exterior light. Exterior light does not always contain light that is emitted from the infrared LED 4 into the window W. It contains natural light, which can transmit through the sensing optical element 2 at an angle not larger than the critical angle, causing little or no internal reflection within the window W.

As can be determined from the foregoing description, the second photoreceptor 6 is designed to measure the amount of natural light. Thus, it can be employed as the exterior light sensor to control a vehicular lamp in response to the brightness of exterior light. The exterior element sensor and the exterior light sensor can be combined by addition of the second photoreceptor 6. Denoted with the reference numeral 9 in FIG. 1 is a circuit board, on which the infrared LED 4, the first photoreceptor 5 and the second photoreceptor 6 can be mounted.

When the second photoreceptor 6 is provided, the light traveling from the external surface toward the second photoreceptor 6 transmits through the connection portion 2b of the sensing optical element 2. As a rule, the light that enters the exterior surface Wo and which transmits through the window W does not interfere with the light that suffers internal reflections in the window W at more than the critical angle (e.g., the infrared light from infrared LED 4). Therefore, the light that enters the exterior surface should not considerably lower the accuracy of the exterior element sensor 1.

In the sensing optical element 2, the incident optical element portion 2a which leads light into the interior surface Wi of the window W at angles larger than the critical angle, and the emissive optical element portion 2c which emits light out of the window W, are provided in the vicinity of the connection portion 2a. Therefore, the infrared LED 4 may possibly interfere with exterior light on an unexpected path.

In the embodiment of FIG. 1, the first photoreceptor 5 can be covered with a black filter 5a, referred to as an infrared transmissive black filter. The black filter 5a transmits infrared therethrough and blocks visible light. Thus, visible exterior light that is used for the exterior light sensor is blocked from leaking into the first photoreceptor 5 so as not to exert an influence on the accuracy of the exterior element sensor 1. The infrared LED 4 may be blinked in certain cycles to distinguish the LED 4 blinked light from naturally occurring infrared light contained in the exterior light. The above-described structures can be interchanged/employed freely.

Figure 2:
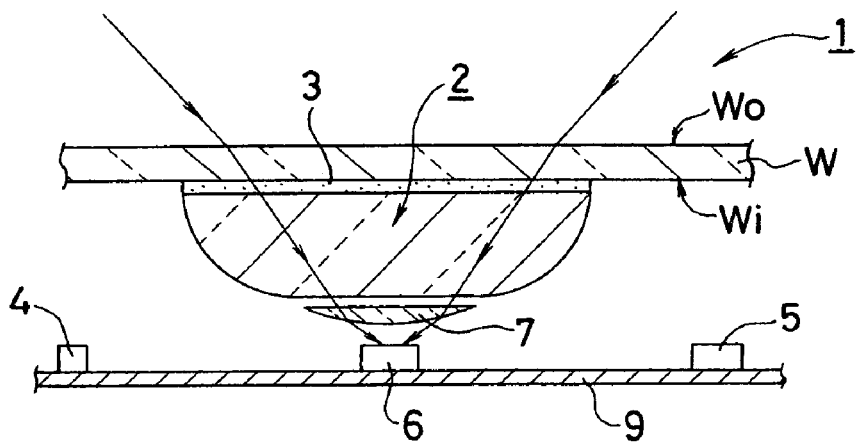
FIG. 2 is a cross-sectional view showing another embodiment of an exterior element sensor made in accordance with the principles of the invention.

FIG. 2 shows another embodiment of an exterior element sensor 1 made in accordance with the principles of the invention. In the preceding embodiment of FIG. 1, the second photoreceptor 6 can be located opposite to the convex side of the connection portion 2b that is formed as a cylindrical lens. In accordance with a characteristic of a cylindrical lens, exterior light converges on the second photoreceptor 6 only in one direction along the axis to lower the efficiency of convergence and lower the efficiency of measurement under a small amount of exterior light.

In the embodiment shown in FIG. 2, an auxiliary lens 7 can be located between the connection portion 2b and the second photoreceptor 6. The auxiliary lens 7 can be a convex lens used for all directional convergence to improve the rate of convergence onto the second photoreceptor 6 and to detect exterior light more sensitively. The auxiliary lens 7 can be provided independently between the connection portion 2b and the second photoreceptor 6 as described above. Alternatively, it may be provided integrally with either the connection portion 2b or the second photoreceptor 6.

Figure 3:
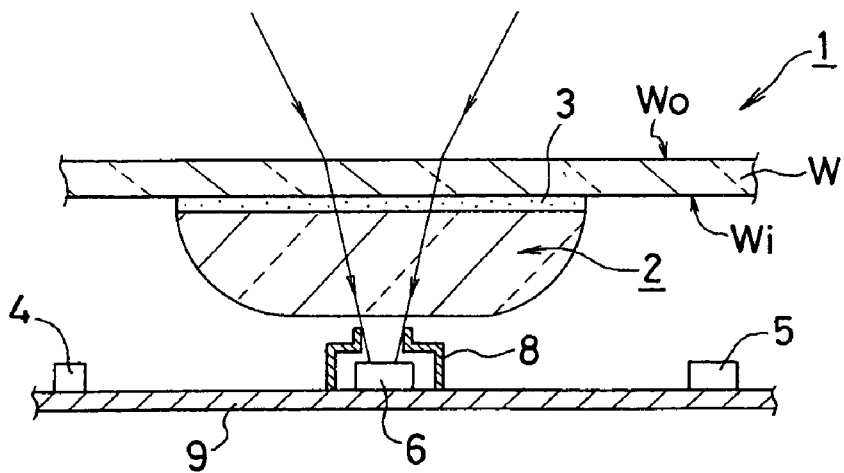
FIG. 3 is a cross-sectional view showing another embodiment of an exterior element sensor made in accordance with the principles of the invention.

FIG. 3 shows another embodiment of an exterior element sensor made in accordance with the principles of the invention. In the embodiment of FIG. 1, the first photoreceptor 5 is covered with the infrared transmissive black filter (black filter 5a) to prevent visible beams from entering the first photoreceptor 5. In the embodiment of FIG. 3, to the contrary, the light that is received from the front direction (among the visible beams of light that enter the exterior surface Wo of the window W) is mainly intended to reach the second photoreceptor 6. The beams that are not from the front direction are not intended to reach the second photoreceptor 6. Namely, the headlight is controlled with reference to exterior light that is received from the front direction of the vehicle. For that purpose, the embodiment of FIG. 3 can include a hood (e.g. a cover 8) composed of an opaque material, or can include the black filter 5a.

The attachment of the black filter 5a, such as the infrared transmissive black filter, to the first photoreceptor 5 as shown in the embodiment of FIG. 1 may be combined with the use of the auxiliary lens 7 in the embodiment of FIG. 2. Alternatively, the attachment of the filter to the first photoreceptor 5 in the embodiment of FIG. 1 may be combined with the attachment of the cover 8 to the second photoreceptor in the embodiment of FIG. 3. Further, the particular structures shown in the embodiments of FIGS. 1-3 may be combined freely.

Figure 4:
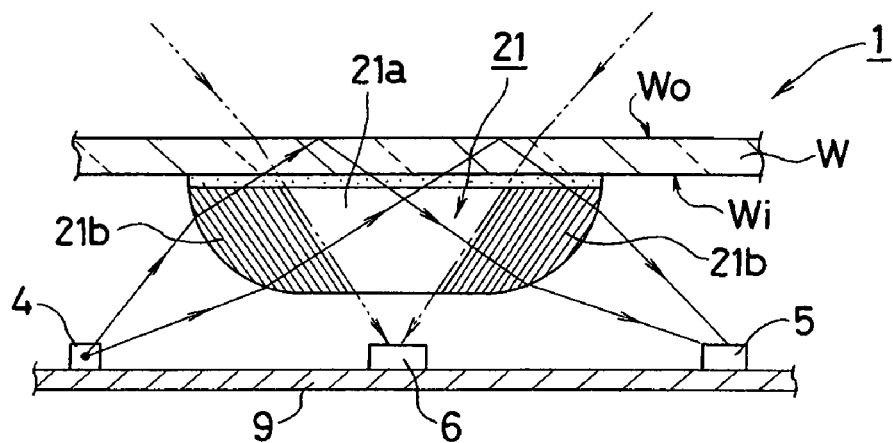
FIG. 4 is an illustrative view showing a portion of another embodiment of an exterior element sensor made in accordance with the principles of the invention.
Figure 5:
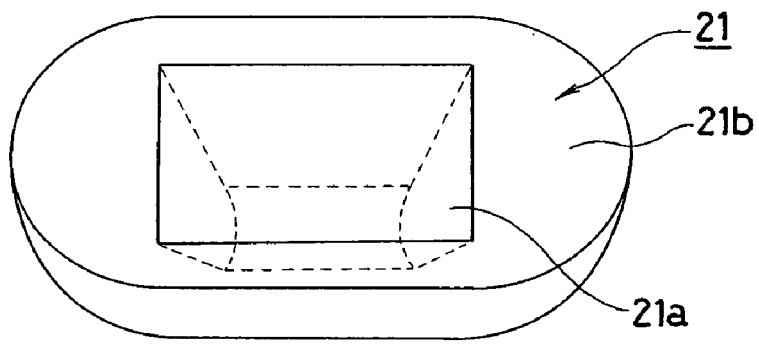
FIG. 5 is a perspective view showing of the embodiment of the exterior element sensor shown in FIG. 4.
Figure 6:
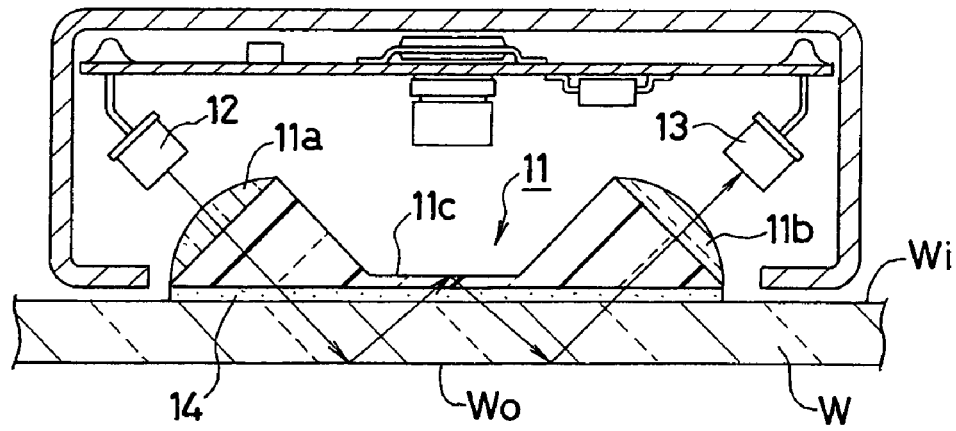
FIG. 6 is an illustrative view showing a related art example of a raindrop sensor.

FIGS. 4 and 5 show another embodiment of an exterior element sensor made in accordance with the principles of the invention. The embodiment shown in FIGS. 4 and 5 is also intended to reduce the interference of the exterior element sensor 1 with the exterior light sensor as one of its many advantages. The configuration of a sensing optical element 21 is devised to provide a more accurate measured result.

In the configuration shown in FIG. 4, infrared light from the infrared LED 4 is employed when the exterior element sensor 1 detects exterior elements (such as raindrops, ice, snow, debris, etc.). The exterior light sensor for setting turn-on timings for the headlight, other lights, or other devices naturally measures the amount of exterior light to prevent the driver from losing the field of vision. The sensing optical element 21 is commonly used in transmission and reflection of infrared and visible beams.

In the embodiment of FIGS. 4 and 5, a visible beam-transmissive portion can be formed as a transparent portion 21a that utilizes a colorless transparent material. The remaining portion can be formed as a black portion 21b of the black filter material for use in formation of the infrared transmissive black filter. As described above, the black material can block visible beams almost completely while having a transmissivity of 90% or more for infrared light. The transparent portion 21a and the black portion 21b can be formed in intimate contact with each other using two-color molding, for example, so as not to cause an air layer and/or a step therebetween.

FIG. 5 is a perspective view showing the shape of the black portion 21b formed of the black material, which is combined with the transparent portion 21a to operate the same as in the sensing optical element 2 described in the embodiment shown in FIG. 4. A contact portion between the transparent portion 21a and the black portion 21b may cause refraction and reflection if both portions have a large difference in refractive index. Therefore, it can be beneficial to employ materials having close refractive index values, like the above.

In accordance with the above described configuration, and in order to remove visible beams, the black portion 21b exists on the optical path along which the infrared light travels to reach the first photoreceptor 5 (after it is internally reflected at the exterior surface of the window W). Although the window W is commonly almost colorless and transparent, visible light coming into this portion can be removed when the light passes through the black portion 21b, so as not to exert an influence on measured results.

On the other hand, the exterior light coming into the window W can transmit through the transparent portion 21a which is in the shape of a horn and surrounded by the black portion 21b. The light can reach the second photoreceptor 6, which measures the amount of exterior light within a certain range in a certain forward direction of the vehicle. Therefore, the angle of the oblique horn-shaped side and the aspect ratio at the lighting portion are adjusted to provide an optimized operation for turning on/off the headlight. Also in the embodiment of FIGS. 4 and 5, the auxiliary lens 7 as described in the embodiment of FIG. 3 may be used together freely.

If the window W has an almost uniform thickness, the light transmitting in a direction that is greater than the critical angle can be propagated within the window W while internally and repeatedly reflected. Accordingly, if the light is reflected from both surfaces of the window W each at least once, that light can be detected similarly if a sensor is attached to either the internal surface or the external surface of the window W.

The above description has been given to the use of the invention for detecting raindrops, water, other fluids, snow, ice, debris, other materials, etc. that is attached to the exterior surface of the window W and for driving the wipers or other device appropriately in accordance with the amount of attached materials to ensure the field of vision is clear. Depending on the vehicle, interior heating in winter may fog over the rear window as is well known. In such a case, a heater-printed rear window (not shown) may be mounted for preventing or removing the fog.

Therefore, the detecting portion in the exterior surface of the window W can be made insensible against attachment of raindrops and/or other materials through processing such as vaporizing aluminum to form a mirror thereon, which allows total reflections to be caused even when raindrops or other materials are present on the window. Thus, occurrence of the fog on the interior surface can be detected and the fog can be removed when the heater is powered on detection of the fog.

While there has been described what are at present considered to be preferred and exemplary embodiments of the invention, it will be understood that various modifications may be made thereto, and it is intended that the appended claims cover all such modifications as fall within the true spirit and scope of the invention.

What is claimed is:

1. An exterior element sensor for use with a window that has an interior surface and an exterior surface, the window separating an exterior atmosphere from an interior atmosphere, comprising:
   a light source capable of emitting light;
   a sensing optical element including
      an incident optical element portion configured to allow the emitted light to enter into the window from the interior surface of the window and at an angle larger than a critical angle, and
      an emissive optical element portion configured to allow the emitted light that is reflected from the exterior surface of the window to exit from the window towards the interior atmosphere, wherein the sensing optical element is located adjacent an incident position of light on the interior surface of the window and an emissive position of light on the interior surface of the window to measure the amount of the light totally reflected from the exterior surface of the window and exiting from the window, thereby measuring an amount of exterior elements located on the exterior surface of the window,
   wherein the sensing optical element of the exterior element sensor further includes a connection portion having one end portion serving as the incident optical element portion and the other end portion serving as the emissive optical element portion, the one end portion and the other end portion both being convex in shape, and a central planar portion of the sensing optical element extends continuously from the one end portion to the other end portion to provide a substantially flat surface between the one end portion and the other end portion;
   a first photoreceptor located opposite to the emissive optical element portion such that it can receive the light that is totally reflected from the exterior surface of the window; and
   a second photoreceptor serving as an exterior light sensor located opposite to the connection portion and between the incident optical element portion and the emissive optical element portion.

2. The exterior element sensor according to claim 1, further comprising:
   a filter attached to the first photoreceptor and configured to block visible light and transmit infrared therethrough.

3. The exterior element sensor according to claim 1, further comprising:
   an auxiliary lens located adjacent the connection portion and configured to condense visible light towards the second photoreceptor.

4. The exterior element sensor according to claim 1, wherein the sensing optical element consists of a transparent material, the exterior element sensor further including a hood composed of an opaque material to set an appropriate light-receiving angle for the second photoreceptor.

5. The exterior element sensor according to claim 1, wherein the sensing optical element has a central portion formed substantially in the shape of a front-wider horn and composed of a transparent material to set an appropriate light-receiving angle for the second photoreceptor, and a peripheral portion composed of a colored material that blocks visible light and transmits infrared light therethrough.

6. The exterior element sensor according to claim 2, further comprising:
   an auxiliary lens located adjacent the connection portion and configured to condense visible light towards the second photoreceptor.

7. The exterior element sensor according to claim 2, wherein the sensing optical element consists of a transparent material, the exterior element sensor further including a hood composed of an opaque material to set an appropriate light-receiving angle for the second photoreceptor.

8. The exterior element sensor according to claim 3, wherein the sensing optical element consists of a transparent material, the exterior element sensor further including a hood composed of an opaque material to set an appropriate light-receiving angle for the second photoreceptor.

9. The exterior element sensor according to claim 2, wherein the sensing optical element has a central portion formed substantially in the shape of a front-wider horn and composed of a transparent material to set an appropriate light-receiving angle for the second photoreceptor, and a peripheral portion composed of a colored material that blocks visible light and transmits infrared light therethrough.

10. The exterior element sensor according to claim 3, wherein the sensing optical element has a central portion formed substantially in the shape of a front-wider horn and composed of a transparent material to set an appropriate light-receiving angle for the second photoreceptor, and a peripheral portion composed of a colored material that blocks visible light and transmits infrared light therethrough.

11. The exterior element sensor according to claim 1, wherein the window is made from glass.

12. The exterior element sensor according to claim 1, wherein the second photoreceptor is mounted in a center between the incident optical element portion and the emissive optical element portion.

13. The exterior element sensor according to claim 2, wherein the filter covers the first photoreceptor.

14. The exterior element sensor according to claim 1, wherein the auxiliary lens is integral with the sensing optical element.

15. The exterior element sensor according to claim 1, wherein a resinous adhesive is located adjacent the sensing optical element for attachment to the window.

16. The exterior element sensor according to claim 1, wherein the exterior elements are raindrops.

17. The exterior element sensor according to claim 1, wherein the light source is an infrared light emitting diode.

18. The exterior element sensor according to claim 1, further comprising:
a cover substantially surrounding the second photoreceptor, the cover being composed of an opaque material and configured to set an appropriate light-receiving angle for the second photoreceptor.

19. The exterior element sensor according to claim 1, wherein the optical element includes two partially spherical portions separated by the connection portion.

20. The exterior element sensor according to claim 1, wherein the first photoreceptor is configured to determine an amount of exterior elements on the window and to control a wiper device for the window in accordance with the determined amount of exterior elements, and the second photoreceptor is configured to determine an amount of the exterior light and control a lighting device in accordance with the determined amount of the exterior light.

* * * * *